(12) United States Patent
Kim et al.

(10) Patent No.: US 11,517,745 B2
(45) Date of Patent: Dec. 6, 2022

(54) ARTIFICIAL RETINA SYSTEM FOR IMPROVING CONTRAST SENSITIVITY

(71) Applicants: KOREA UNIVERSITY RESEARCH AND BUSINESS FOUNDATION, Seoul (KR); GACHON UNIVERSITY OF INDUSTRY-ACADEMIC COOPERATION FOUNDATION, Gyeonggi-do (KR)

(72) Inventors: Seong-woo Kim, Seoul (KR); Jungsuk Kim, Gyeonggi-do (KR)

(73) Assignees: GACHON UNIVERSITY OF INDUSTRY-ACADEMIC COOPERATION FOUNDATION, Gyeonggi-Do (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 622 days.

(21) Appl. No.: 16/490,846

(22) PCT Filed: Mar. 8, 2018

(86) PCT No.: PCT/KR2018/002740
§ 371 (c)(1),
(2) Date: Sep. 3, 2019

(87) PCT Pub. No.: WO2018/174439
PCT Pub. Date: Sep. 27, 2018

(65) Prior Publication Data
US 2020/0001072 A1    Jan. 2, 2020

(30) Foreign Application Priority Data
Mar. 23, 2017    (KR) .................. 10-2017-0037035

(51) Int. Cl.
*A61N 1/05* (2006.01)
*A61F 2/14* (2006.01)
*A61N 1/36* (2006.01)

(52) U.S. Cl.
CPC .............. *A61N 1/0543* (2013.01); *A61F 2/14* (2013.01); *A61N 1/36046* (2013.01);
(Continued)

(58) Field of Classification Search
CPC .............. A61N 1/0543; A61N 1/36046; A61N 1/36128; A61N 1/36192; A61N 1/3615; A61F 2/14; A61F 2250/0002
See application file for complete search history.

(56) References Cited

U.S. PATENT DOCUMENTS 6,608,296 B1    8/2003   Toyoda et al.
7,244,919 B2    7/2007   Ishikawa et al.
(Continued)

FOREIGN PATENT DOCUMENTS

JP    2004024342    * 1/2004
KR    20030071230    9/2003
(Continued)

*Primary Examiner* — William H Matthews
(74) *Attorney, Agent, or Firm* — Fay Kaplun & Marcin, LLP

(57) ABSTRACT

Provided is an artificial retina system for improving contrast sensitivity. The artificial retina system includes an artificial retina which is installed under the retina and includes a plurality of photodiode cells and a microcomputer. The microcomputer compares, with at least one reference value, the magnitude of an electric signal outputted from a photodiode in each of the photodiode cells. The microcomputer controls to amplify or reduce the electric signal outputted by each of the photodiode cells according to the result of comparison. Visual cells corresponding to each of the pho-
(Continued)

todiode cells can be stimulated with an electric signal controlled by the microcomputer.

8 Claims, 8 Drawing Sheets

(52) U.S. Cl.
CPC ..... *A61N 1/36128* (2013.01); *A61N 1/36192* (2013.01); *A61F 2250/0002* (2013.01); *A61N 1/3615* (2013.01)

(56) References Cited

U.S. PATENT DOCUMENTS

| | | |
|---|---|---|
| 2010/0241192 A1 | 9/2010 | Greenwald et al. |
| 2012/0029304 A1* | 2/2012 | Medina ................ A61B 5/0002 600/300 |
| 2013/0218271 A1 | 8/2013 | Wu et al. |
| 2014/0031931 A1* | 1/2014 | Liran ........................ A61F 2/14 623/6.63 |
| 2014/0031934 A1 | 1/2014 | Liran et al. |
| 2015/0256779 A1* | 9/2015 | Haraguchi ......... H04N 5/37457 348/308 |

FOREIGN PATENT DOCUMENTS

| | | |
|---|---|---|
| KR | 101275215 | 6/2013 |
| KR | 20160045530 | 4/2016 |
| WO | 2018/105940 | 6/2018 |

\* cited by examiner

ARTIFICIAL RETINA SYSTEM FOR IMPROVING CONTRAST SENSITIVITY

TECHNICAL FIELD

The present invention relates to an artificial retina system with improved contrast sensitivity compared to a related artificial retina.

BACKGROUND ART

The retina is an important neuronal tissue that converts the external image incoming through the cornea and lens into an electrical signal and transmits the electrical signal to the brain. The width of the retina is about 6.25 $cm^2$, and there are about 100 million visual cells in the retina. The rod cells, which occupy the majority of the visual cells layer, convert the image into electric signals, and these electric signals enter the optic neuronal and are transmitted to the brain at a speed of about 480 km/h. The brain interprets the minute electrical signals, perceives images, and determines objects. The retina is one of the tissues with the largest blood supply per unit area and needs to be removed smoothly of wastes generated as a byproduct of the chemical action. For any reason, when abnormalities occur in the retinal blood vessels or choroidal blood vessels, an abnormality occurs in the retina, which causes various diseases.

Retinitis pigmentosa (RP), a retinal disease, is a progressive retinal degenerative disease caused by dysfunction of the photoreceptors distributed in the retina, and is characterized by the retinal photoreceptor and retinal pigment epithelium as the main lesion and an occurrence in both eyes. The prevalence rate of RP is reported to be 1 out of 5,000 worldwide. Age-related macular degeneration (AMD), which is another type of retinal disease, is one of the three major blindness diseases, and is a trend in which the prevalence rate is rapidly increasing due to the rapid aging of the population. It has been reported that patients with AMD are more likely to have worsened vision in a relatively short period of time, unlike patients with low vision due to RP disease, and the degree of actual life impairment and psychological atrophy caused by the eye in patients with AMD is greater than those caused by other diseases.

In order to treat patients with blindness, various therapies such as gene therapy, stem cells, and drug therapy have been attempted. Meanwhile, most patients with blindness often have already damaged retinal visual cells layer and are most likely to be out of time for gene therapy or medication, in many cases. However, in the case of geriatric diseases such as RP and AMD, since only the visual cells layer, which is the outer layer of the retina, is damaged, there is a possibility of vision recovery if the function of the visual cells layer is replaced. Therefore, the artificial retina that induces electric stimulation to the visual cells layer of the retina to restore the vision for the patients with blindness is a promising new therapy.

Referring to FIG. 1, the artificial retina may be classified into epi-retinal and sub-retinal types depending on the locations of installation. The epi-retinal type is located in front of the retina and the sub-retinal is located on the visual cells layer behind the retina. The epi-retinal type artificial retina stimulates the ganglion cell layer among the retinal cells and the sub-retinal type artificial retina stimulates the bipolar cell layer in the posterior side. The epi-retinal type artificial retina has a neural cell stimulator located in front of the retina, and thus, the intermediate signal processing of neuronal cells in the inner retina is not carried out. Therefore, the epi-retinal type artificial retina is equipped with an external camera separately. The external camera is built in the glasses and provided, and the image information obtained from the camera reaches the intraocular microelectrode array wirelessly through the induction coil, and directly stimulates the retinal ganglion cells without intermediate signal processing of the neurons cells in the inner retina. Meanwhile, the threshold value for responding electric stimulation varies depending on the patient, and the magnitude of electric stimulation to be applied also varies according to the retinal cell damage region. The epi-retinal type artificial retina has a method of independently controlling the electrodes in the external image processor. Therefore, there is an advantage that the magnitude of the electric pulse may be freely changed according to the patient or the damaged region.

As a related art, in the case of Argus II product commercially available by Second Sight in the US, 64 electrodes can be independently controlled, and the magnitude of electrical stimulation generated from the electrodes is also controllable. However, in the case of the epi-retinal type artificial retina, there is a disadvantage that it is difficult to affix the electrode considering that the retina is very thin and weak. In addition, being located inside the retina, it may be exposed to the vitreous body, and also, since it is surrounded by the fibrous tissue, there is a possibility that the electric stimulation is not transmitted. In addition, there is a disadvantage that, when electrical stimulation is applied on the upper side of the retina, it is difficult to improve the spatial resolution because the retinal neural fiber layer is stimulated, spreading the signals, or the cells of several layers of the retina are simulated at once. Since the epi-retinal type artificial retina may not utilize the signal processing within the retina, the shape of the stimulating electrode grid and the shape actually perceived by the patient may be different from each other, and this accordingly requires a customized image processing for each patient. Therefore, there is a disadvantage that a variety of components, and a signal transmission unit for connecting these are required compared to a sub-retinal type artificial retina.

In the sub-retinal type artificial retina, the photodiode array is located on the photoreceptor cell layer below the retinal cell layer. The sub-retinal type artificial retina was designed to simply replace the function of the photoreceptor, and the bipolar cell is the primary electrical stimulus target. To this end, the sub-retinal type artificial retina is designed to integrate photodiodes for sensing light and electrodes for stimulation, and stimulate the retinal neuronal cells by flowing the current from the photodiode directly toward the electrode. The photodiode array performs similar functions as a CMOS image sensor. The magnitude of the dark current generated in each photodiode cell varies depending on the intensity of the light, and this current is changed into a biphasic current pulse through the conversion circuit, to act as an active potential. The advantage of the sub-retinal type artificial retina is that it utilizes the existing visual transmission path through the information processing of the bipolar cell and the retinal inner layer, thereby giving the natural feeling in perceiving objects. In addition, the microelectrode array is inserted into the eyeball, allowing natural eye movement, which can be said to be advantageous in terms of physiological and natural manner, compared to a system with a compact camera built in glasses, which requires a user to turn his or her head, not the eyes, in the direction of an object in order to look and perceive the object. Further, since the greatest number of pixels are produced by the sub-retinal type stimulation method among artificial retinas created so far, this suggests a possibility of achieving high resolution.

As another related art, the Alpha IMS model, which was successfully commercialized by Retina Implant in Germany, has a 1500 photodiode array and a matched bi-phasic current generation array corresponding thereto, but it is reported that, according to clinical tests, the actual resolution is lower than the resolution of the 63 channel epi-retinal type artificial retina. When the epi-retinal type artificial retina is stimulated, an image captured by the camera is converted into a digital signal through image processing and then is converted into a serial digital signal through encoding to be transmitted the artificial retina.

Both of the above products currently available in surgery merely serve to convert the light on the visual cells into an electric signal to generate electric current and transmit the signal to the optic nerves using the existing living retinal structures. However, while RP or AMD is a disease from which primarily visual cell layers are lost and then the vision is lost, in many actual cases of patients with blindness, the remaining neural transmission layer in the retina, for example, bipolar cells, horizontal cells, and the like are also lost as the secondary changes. In FIG. 2, the horizontal cells do not directly transmit the current stimulus generated in the visual cells to the neuronal fiber layer of the retinal ganglion cell, but they serve to control the intensity of the current in the transmission process to help to more clearly distinguish the contrast of the object, and serve to increase the contrast sensitivity of the object in the brain. The reason why contrast sensitivity is important in vision is that it plays an important role in distinguishing and perceiving the shape (for example, two-dimensional information such as a face shape, or the like, a three-dimensional, stereoscopic shape including a shadow) of an object more clearly from the background. That is, there is a physiological circuit which, when the neuronal cells are excited, transmits the inhibitory neurotransmitter to the neighboring neuronal cells through the horizontal cells to make the neighboring neuronal cells to be less active, which is explained as a mechanism for clearly perceiving the boundary. This is referred to as lateral inhibition by the horizontal cells.

Referring to FIG. 2, the horizontal cell extends the process in the tangential plane of the retina side by side with the optic neuronal fibers. Thin and long dendrites are ends at the axon of rod cells and cone cells, and thin cell bodies are located in the inner granular layer.

Referring to FIG. 3A, a cone cell that does not receive the light of the surround is in a depolarized state as usual, and secretes glutamate, which excites the off ganglion cells in succession through the off bipolar cells to cause a person to feel that the surrounding area is dark. In this process, the depolarized visual cells in the surround excite horizontal cells in the area. The excited horizontal cells receiving adjacent light further hyperpolarize the already hyperpolarized center visual cells to inhibit the secretion of glutamate and excite the on ganglion cells in succession through the on bipolar cells to cause a person to feel that the corresponding central area is bright. Referring to FIG. 3B, when light enters the surround, the visual cells are hyperpolarized to inhibit the secretion of glutamate, and excite the on ganglion cell in succession through the connected on bipolar cells to cause a person to feel that the corresponding surrounding area is bright. In this process, the hyperpolarized visual cells of the surround cannot excite the horizontal cells of the surround, and the cone cells not receiving the light of the adjacent center are in the depolarized state as usual, and have no influence on the secretion of glutamate. That is, as the off ganglion cells are excited in succession through the connected off bipolar cells, a person feels that the central region is dark.

At present, the epi-retinal type artificial retina product that collects visual information from an artificial retina system with an external camera is able to independently adjust the intensity of the electric current stimulating the inside of the eye by processing information with a camera image analysis program, but with the sub-retinal type artificial retina or the like, which simply applies the output current to the visual cells using photodiodes, the difference in current generated in contrast to the contrast is not large enough for a patient to have the contrast sensitivity.

CITATION LIST

Patent Literature (PTL 1) Korean Patent Publication No. 10-2016-0045530 (2016 Apr. 27)

(PTL 2) Korean Patent Publication No. 10-1275215 (2013 Jun. 17)

SUMMARY OF INVENTION

The present invention relates to an artificial retina system that collects the magnitudes of the stimulation currents generated by the photodiode array stimulators used in the sub-retinal type artificial retina, and compares the collected magnitudes of the currents with the magnitude of the current generated by the adjacent stimulator (or with its own threshold voltages) and amplifies the difference to increase contrast sensitivity.

An artificial retain system for improving contrast sensitivity according to an embodiment of the present invention is provided, which may include an artificial retina 100 which is installed under a retina and includes a plurality of photodiode cells 110, and a microcomputer 200 that compares a magnitude of an electric signal output from a photodiode 111 in each of the photodiode cells 110 with at least one reference value, and controls to amplify or attenuate the electric signal output from each of the photodiode cells 110 according to the result of the comparison, in which visual cells corresponding to each of the photodiode cells 110 may be stimulated with an electric signal controlled by the microcomputer 200.

In an embodiment, it is preferable that the photodiode cells 110 include the photodiode 111 that converts light introduced from outside into an electric signal and outputs the electric signal, a copier 112 that copies the electric signal output from the photodiode 111, an amplifier 113 that amplifies or attenuates the electric signal output from the copier 112, and a stimulation electrode 115 that stimulates the visual cells with the electric signal output from the amplifier 113, in which the microcomputer 200 may adjust gain of the amplifier 113 to control to amplify or attenuate the electric signal output from the photodiode cell 110.

In an embodiment, it is preferable that each of the photodiode cells 110 further includes a converter 114 that causes the electric signal output from each of the photodiode cells 110 to have a form of a biphasic electric signal.

In an embodiment, it is preferable that the microcomputer 200 stores a gain value corresponding to a value equal to or greater than one of the at least one reference value and less than another reference value, and when the number of the at least one reference value is N, the number of the gain values is N+1.

In an embodiment, it is preferable that the microcomputer 200 includes a transimpedance amplifier 210 that converts the electric signal copied by the copier 112 into a voltage signal, a comparator 220 that compares a magnitude of the voltage converted by the transimpedance amplifier 210 with the threshold value, a controller 230 that controls the amplifier 113 in accordance with the result of the comparison by the comparator 220, and a memory 240 that stores a gain value of the amplifier 113 determined by the controller 230.

In an embodiment, it is preferable that the artificial retina system for improving contrast sensitivity further includes a user input unit 500 that receives a user command, and an external computer 600 that executes the microcomputer 200 according to the user command.

In an embodiment, it is preferable that the microcomputer 200 further includes a communication unit 250 that wirelessly communicates with the external computer 600.

Further, an artificial retina system for improving contrast sensitivity according to the present invention is provided, which may include an artificial retina 100 which is installed under a retina and includes a plurality of photodiode cells 110, and a microcomputer 200 that compares a magnitude of an electric signal flowing from one photodiode 111a of each of the photodiode cells 110 with a magnitude of an electric signal flowing from another photodiode 111b adjacent to the photodiode 111a, and controls to amplify or attenuate an electric signal output from each of the photodiode cells 110 in accordance with the result of the comparison, in which visual cells corresponding to each of the photodiode cells 110 may be stimulated with the electric signal controlled by the microcomputer 200.

In an embodiment, it is preferable that the microcomputer 200 controls switches $S_1$ and $S_2$ connected to stimulation electrodes 115a and 115b of the photodiode cells 110 in accordance with the result of the comparison, to control to amplify or attenuate the electric signal output from each of the photodiode cells 110.

In an embodiment, it is preferable that the microcomputer 200 closes the switch $S_2$ connected to the photodiode 111b that outputs a larger electric signal, and opens the switch $S_1$ connected to the photodiode 111a that outputs a smaller electric signal.

Further, an artificial retina system for improving contrast sensitivity according to the present invention is provided, which may include an artificial retina 100 which is installed under a retina and includes a plurality of photodiode cells 110, and a microcomputer 200 that compares a magnitude of an electric signal flowing from a photodiode 111 of each of the photodiode cells 110 with at least one reference value and controls such that a current is output through a current generator 260 in accordance with the result of the comparison, in which visual cells corresponding to each of the photodiode cells 110 may be stimulated with the current controlled by the microcomputer 200.

According to the present invention, it is possible to provide an artificial retina having improved contrast sensitivity by comparing the magnitudes of the electric currents generated in the photodiodes and controlling the corresponding gain of the amplifier.

Since the contrast sensitivity is improved, there is an advantage that it is possible to perceive the interface between the background image and the object more clearly and to minimize the cross talk phenomenon, thereby providing an optimal resolution for the patient equipped with the artificial retina.

DESCRIPTION OF EMBODIMENTS

1. Artificial Retina System According to First Embodiment

Figure 1:
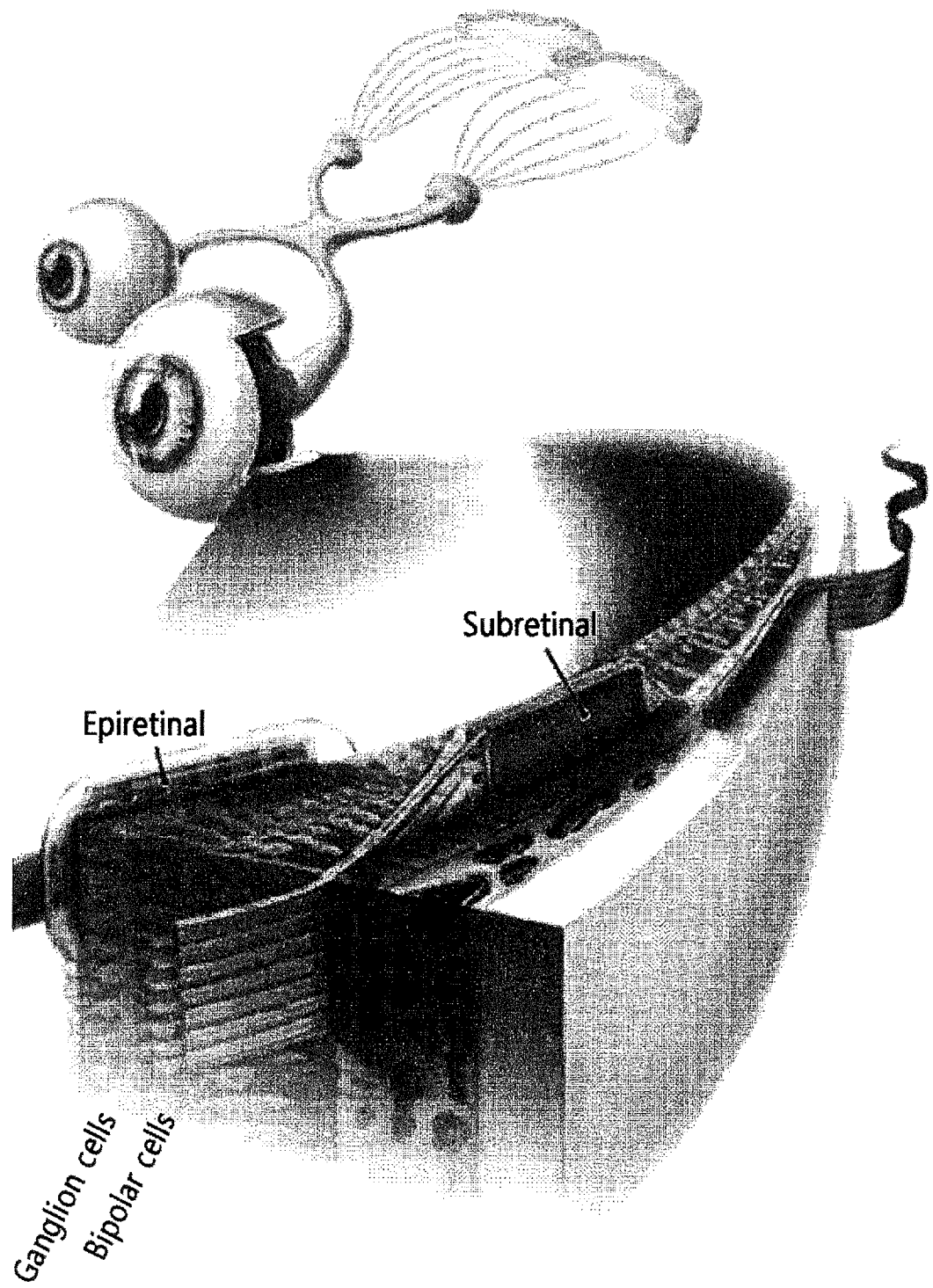
FIGS. 1 and 2 are views for explaining the structure of the retina.
Figure 2:
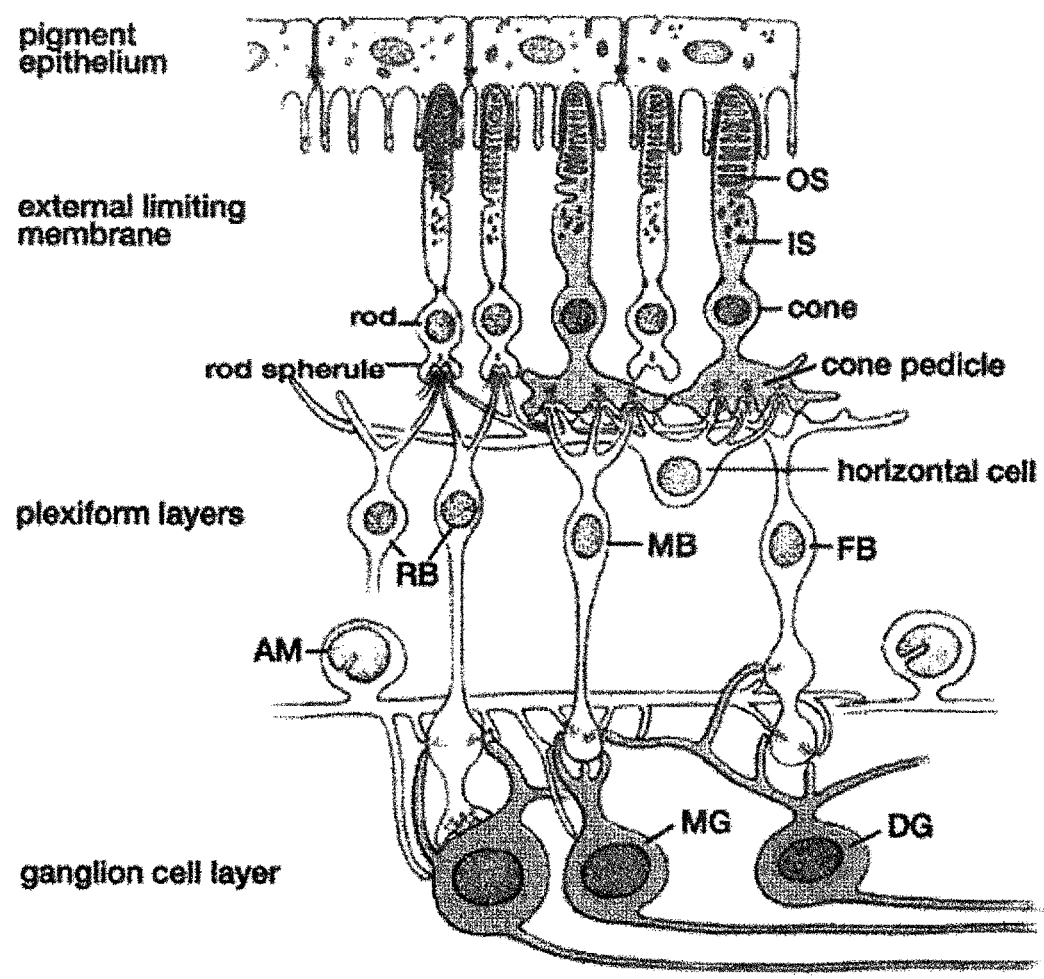
Figure 3:
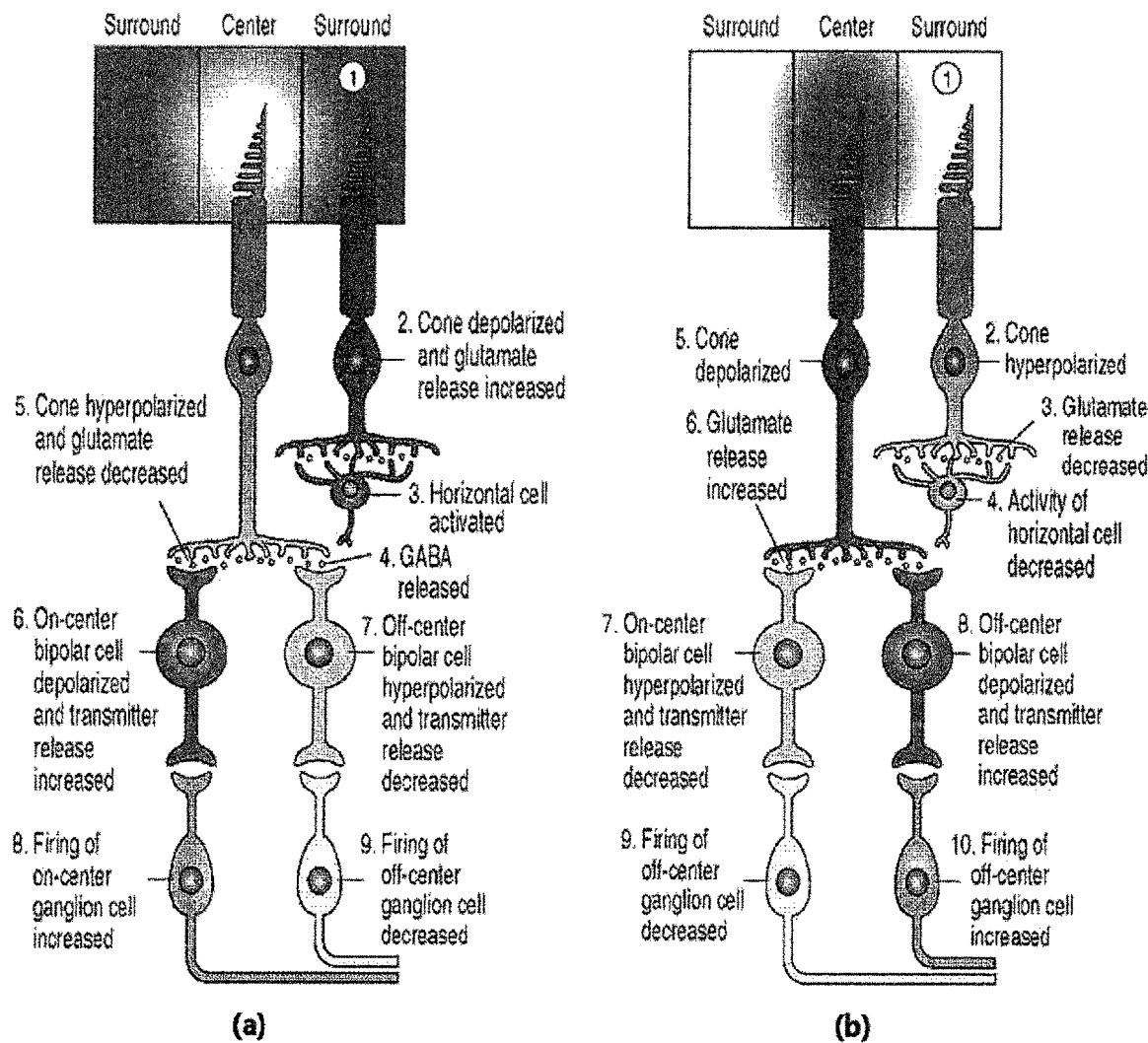
FIG. 3 is a view for explaining the lateral inhibition phenomenon by the horizontal cells that improve contrast sensitivity of the retinal cells.
Figure 4:
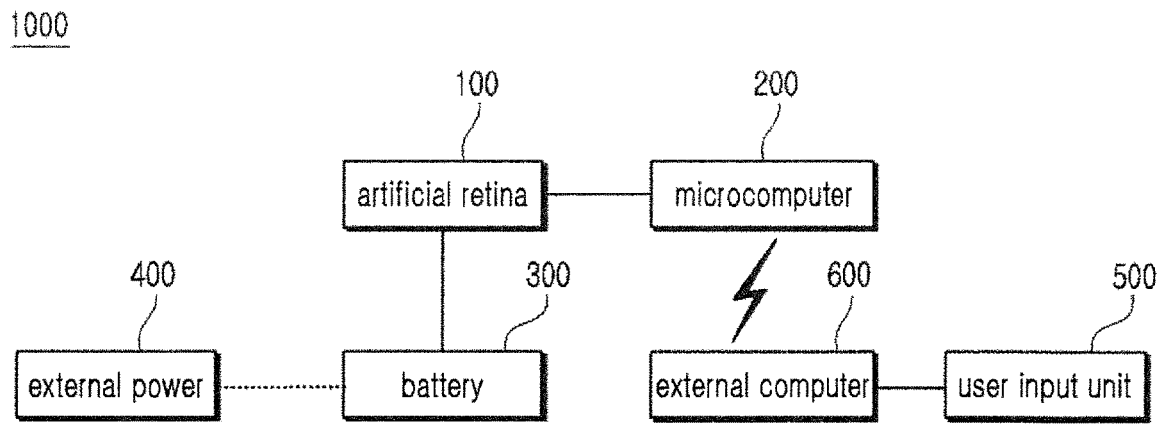
FIG. 4 is a block diagram illustrating an artificial retina system according to an embodiment of the present invention.

First, an artificial retina system according to a first embodiment of the present invention will be described with reference to FIG. 4. FIG. 4 is a diagram illustrating the overall configuration of an artificial retina system. The artificial retina system according to the present invention includes an artificial retina 100, a microcomputer 200, a battery 300, an external power 400, a user input unit 500, and an external computer 600.

The artificial retina 100 is a part which is installed on the visual cells layer of the retina and converts the light into an electric signal to stimulate the visual cells V with the converted electric signal, and the artificial retina 100 will be described in detail below.

The microcomputer 200 is a part which controls each of the photodiode cells 110 of the artificial retina 100, and, specifically, it is a part that compares the magnitude of the electric signal flowing from a photodiode 111 with reference values $R_1$ and $R_2$, and controls to amplify or attenuate the electric signal output from each of photodiode cells 110 based on the result of the comparison. In this example, the control to amplify or attenuate the electric signal is performed by adjusting the gain of an amplifier 113 of the photodiode cell 100, and this process of gain adjustment by the microcomputer 200 will be described below.

The battery 300 is a part that supplies power to the artificial retina 100 and the microcomputer 200. The battery 300 is inserted into the human body, connected to the artificial retina 100 and the microcomputer 200 through a cable, and charged by resonance with an external power 400 located outside the human body. The charging process of the battery 300 by the external power 400 is not a feature of the present invention, so a detailed description thereof will be omitted.

The external computer 600 is a part that controls the artificial retina 100 and the microcomputer 200 from outside through communication with the microcomputer 200. It is possible to turn on/off each of the photodiode cells 110 of the artificial retina 100 through the operation of the external computer 600, and it is also possible to operate a switch S.

The user input unit 500 is a part that inputs a command to the external computer 600 through the user input unit 500. The command input through the user input unit 500 and the external computer 600 controls the microcomputer 200.

Figure 5:
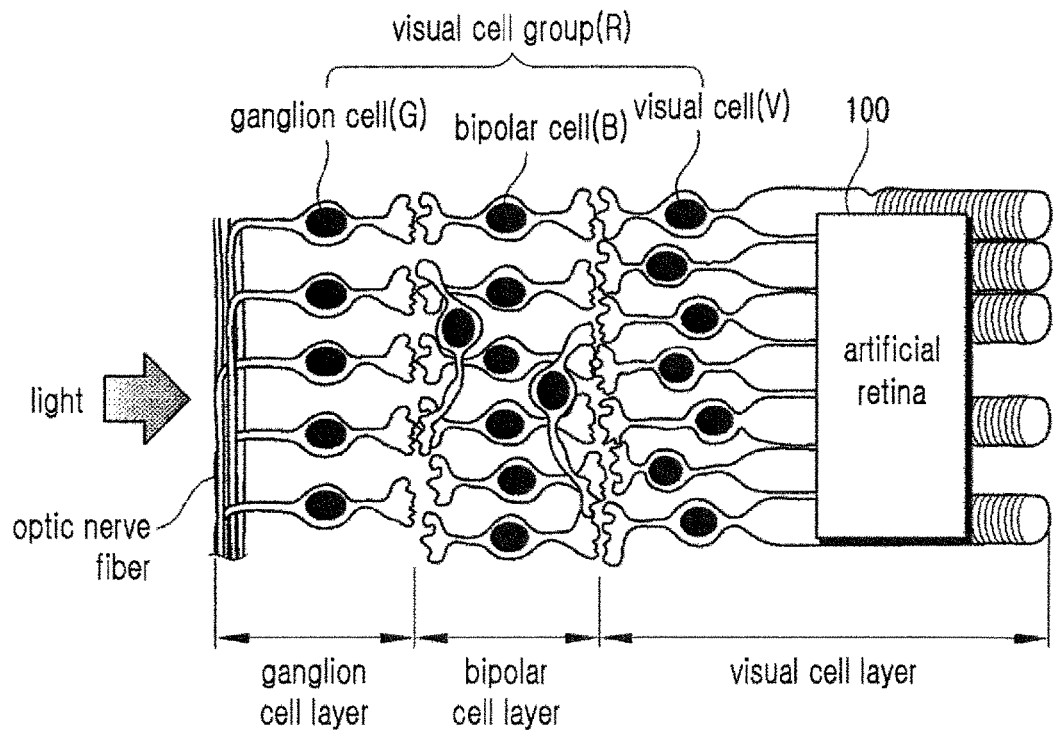
FIG. 5 is a schematic view of a location of an artificial retina according to an embodiment of the present invention.

Next, the artificial retina 100 will be described in detail with reference to FIG. 5. FIG. 5 is a view for explaining a location where the artificial retina 100 is implanted in the retina.

Light introduced into the eyeball from the outside reaches the visual cells through the ganglion cells and bipolar cells, and the visual cells V convert the light into electric signals to stimulate the bipolar cells B. These electric signals then travel through the bipolar cells B and the ganglion cells G, and then through the optic neuronal fibers connected to the ganglion cells G to be transmitted to the brain, which perceives the vision. However, patients with RP or AMD disease cannot perceive vision because these visual cells layer is damaged and cannot function properly. The artificial retina is a device that replaces damaged visual cells, which converts light introduced from the bipolar cells into electric signals to stimulate the visual cells to restore vision.

Referring to FIG. 5, the artificial retina 100 is installed on the visual cells layer and electrically stimulates, with an electric signal, the visual cells V corresponding to the artificial retina 100. The artificial retina 100 is provided in the form of a chip, and a plurality of photodiode cells 110 are provided on the chip. Resolution of the implanted artificial retina 100 is proportional to the number of pixels of the photodiode cells. That is, the larger the number of the photodiode cells, the higher the resolution performance.

Figure 6:
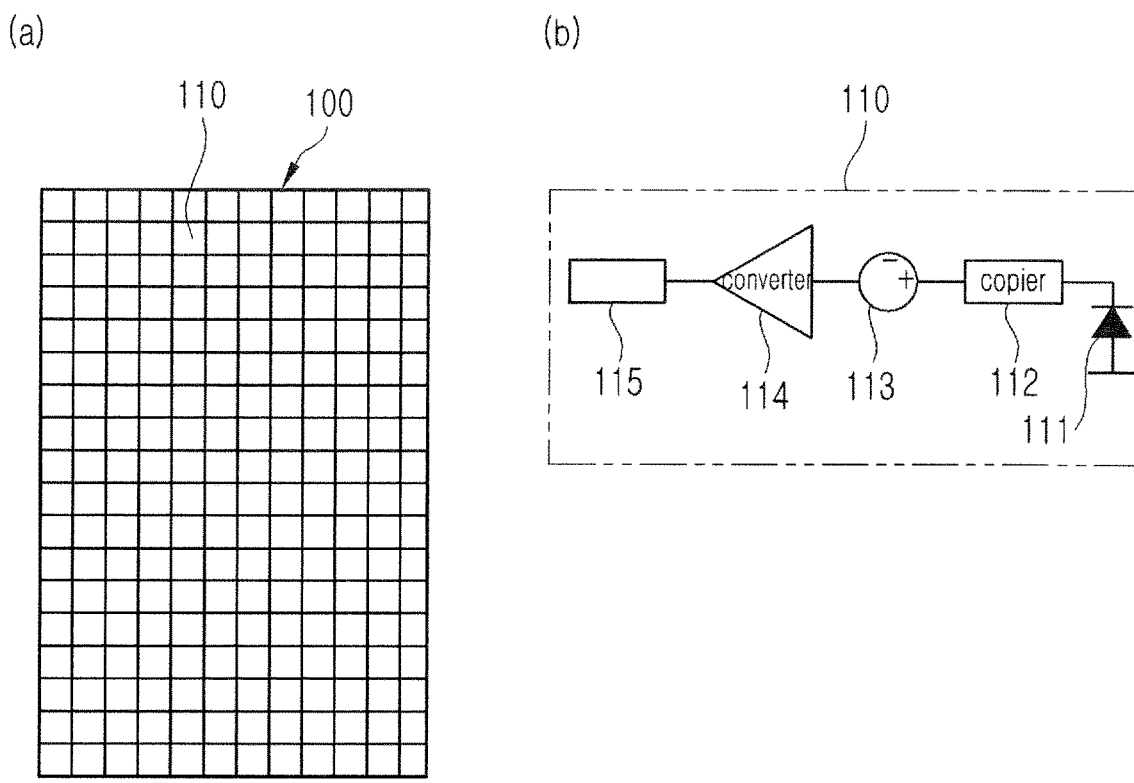
FIG. 6 is a conceptual diagram for explaining a structure of an artificial retina according to an embodiment of the present invention.

The photodiode cell 110 will be described in detail with reference to FIG. 6. Referring to FIG. 6, the photodiode cell 110 includes a photodiode 111, a copier 112, an amplifier 113, a converter 114, and a stimulation electrode 115.

The photodiode 111 is a part that senses the light introduced from the outside and converts the light into an electric signal corresponding thereto and outputs the same.

The electric signal converted by the photodiode 111 is copied by a copier 112. One of the electric signals copied by the copier 112 flows into an amplifier 113 and the other flows into a transimpedance amplifier 210 of the microcomputer 200 to be described below.

The electric signal flowing into the amplifier 113 is amplified or attenuated by the amplifier 113. The gain of the amplifier 113 is adjusted by the microcomputer 200 described below and it is possible to electrically stimulate the visual cells V by controlling the gain of the amplifier 113 so that the contrast sensitivity is improved.

The converter 114 is a part that converts the electric signal amplified or attenuated by the amplifier 113 into a biphasic current pulse corresponding thereto. This is a part that makes the electric signal output from the photodiode cell 110 in the form of a biphasic electric signal, as the electric signal past through the amplifier 113 alone cannot stimulate the visual cells V and it is thus necessary to convert it into a biphasic current pulse by the converter 114. The converter 114 generates a biphasic current pulse corresponding to the magnitude and duration of the electric signal past through the amplifier 113.

The stimulation electrode 115 is a part that stimulates the visual cells V with the biphasic current pulse generated by the converter 114. This is a part that stimulates the visual cells V with an electric signal output from the photodiode cell 110, and the patient with the artificial retina 100 can have a restoration of the vision by the stimulating electrode 115 stimulating the visual cells V.

Next, the microcomputer 200 will be described in detail with reference to FIGS. 7 to 9.

Figure 7:
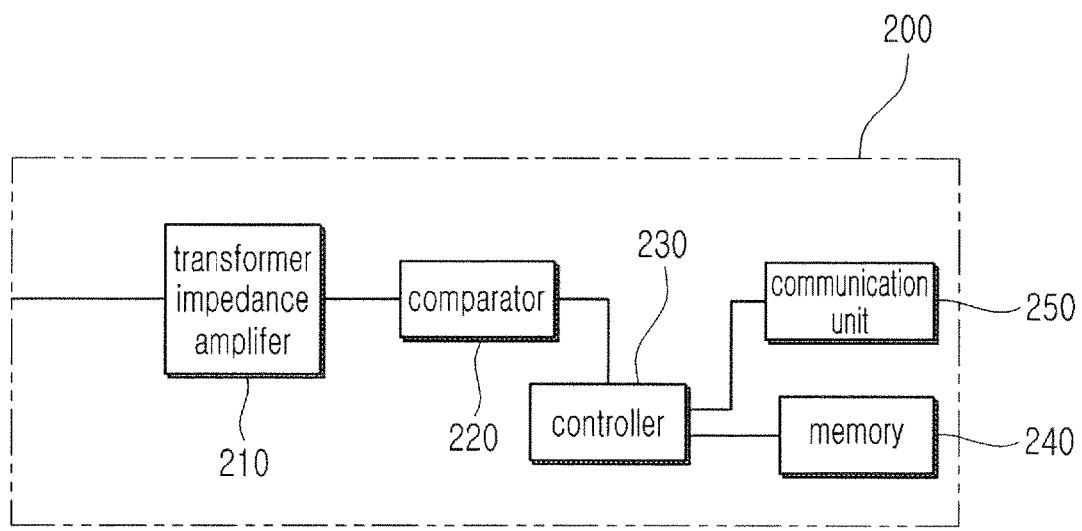
FIG. 7 is a block diagram for explaining a configuration of a microcomputer according to an embodiment of the present invention.

Referring to FIG. 7, the microcomputer 200 includes a transimpedance amplifier 210, a comparator 220, a controller 230, a memory 240, and a communication unit 250. Specifically, this is a part that compares the magnitude of the electric signal flowing from the photodiode 111 with the reference values $R_1$ and $R_2$, and controls, through gain control of the amplifier 113, to amplify or attenuate the electric signal output from each of the photodiode cells 110 based on the result of the comparison.

Figure 8:
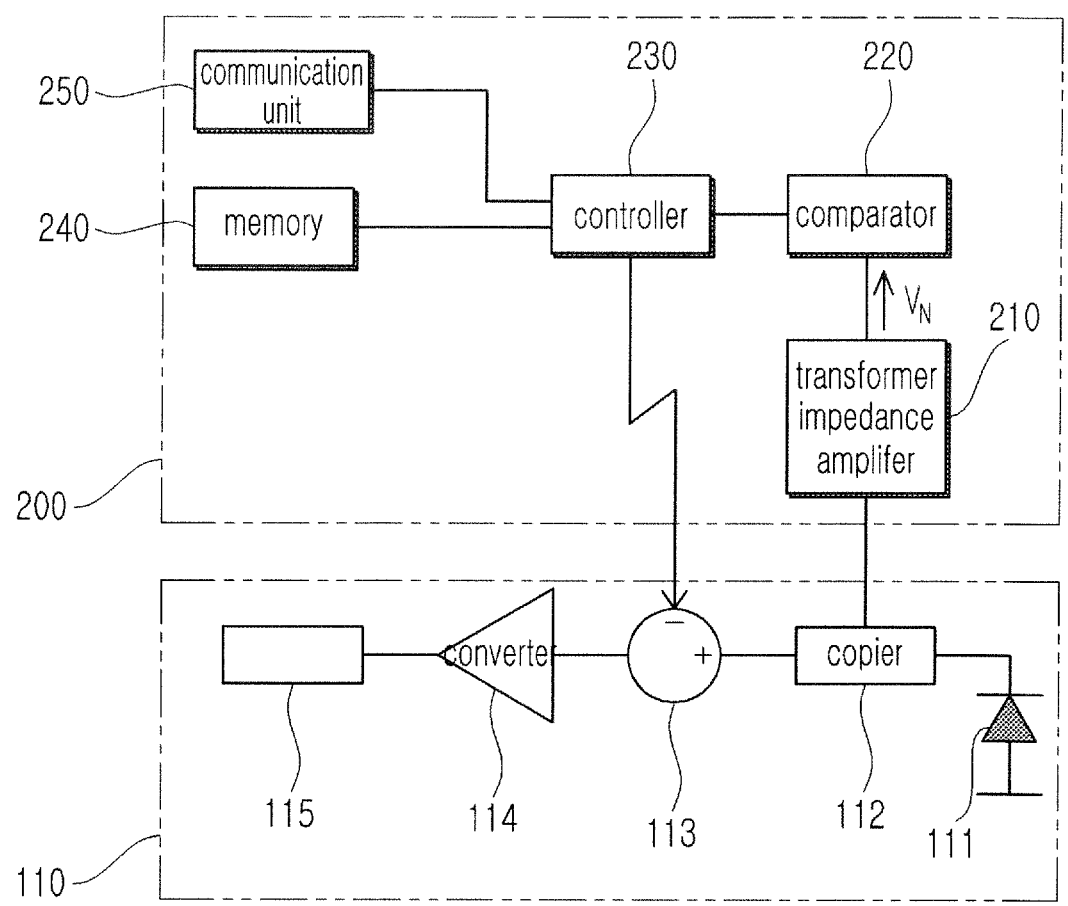
FIG. 8 is a diagram for explaining an operation of an artificial retina system according to an embodiment of the present invention.
Figure 9:
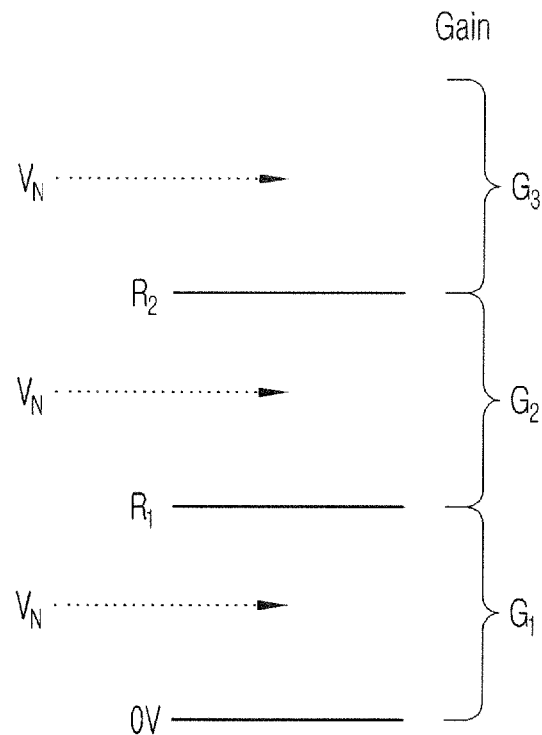
FIG. 9 is a diagram for explaining an operation of a comparator of the artificial retina system of FIG. 8.

Referring to FIGS. 8 and 9, a process of comparing the magnitude of the electric signal with the reference values $R_1$ and $R_2$ and adjusting the gain of the amplifier 113 will be described.

When light enters the eyeball from the outside, the photodiode 111 of each of the photodiode cells 110 outputs an electric signal corresponding to the magnitude of the introduced light.

The electric signals output from the photodiode 111 are copied by the copier 112, and at this time, one of the copied electric signals flows into the amplifier 113 and the other flows into the transimpedance amplifier 210.

The electric signal flowing into the transimpedance amplifier 210 is converted into a voltage signal $V_N$ by the transimpedance amplifier 210. The voltage signal $V_N$ converted by the transimpedance amplifier 210 flows into the comparator 220.

The comparator 220 compares the voltage signal $V_N$ with the predetermined reference values $R_1$ and $R_2$. In this example, the reference values $R_1$ and $R_2$ are stored in the memory 240 in advance. In the present description, it is exemplified that there are two reference values, but the number of reference values is not limited. Since the larger number of reference values enables the more precise gain adjustment, the further improved contrast sensitivity can be provided. Referring to FIG. 9, when there are two reference values, there are three gain values of the amplifier 113. In other words, when there are N reference values, there are N+1 gain values of the amplifier 113.

When the voltage signal $V_N$ is greater than 0 and less than $R_1$, the gain value is $G_1$, when the voltage signal $V_N$ is greater than $R_1$ and less than $R_2$, the gain value is $G_2$, and when the voltage signal $V_N$ is greater than $R_2$, the gain value is $G_3$.

The gain of the amplifier 113 is adjusted through the controller 230 based on the result of the comparison of the voltage signal $V_N$ and the reference value through the comparator 220. That is, the controller 230 adjusts the gain of the amplifier 113 of each of the photodiode cells 110 through the gain value assigned by the comparator 220. Each of the photodiode cells 110 stimulates the visual cells V with electric signals having different magnitudes according to the magnitude of the introduced light, so that the contrast sensitivity of a patient with the artificial retina 100 can be improved.

2. Artificial Retina System According to Second Embodiment

Figure 10:
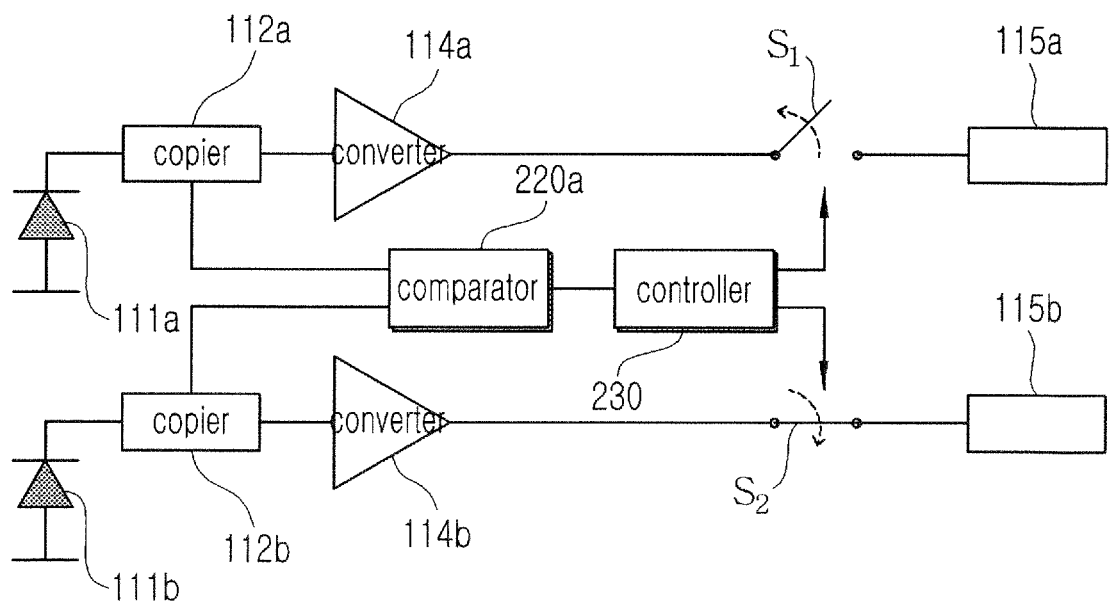
FIG. 10 is a diagram for explaining an operation of an artificial retina system according to another embodiment of the present invention.

The artificial retina system according to the second embodiment of the present invention will be described with reference to FIG. 10. In the artificial retina system according to the first embodiment, the electric signal output from the photodiode 111 of each of the photodiode cells 110 is compared with a reference value, and the amplifier 113 is adjusted to have the gain value corresponding thereto, thus improving the contrast sensitivity, but in the artificial retina system according to the second embodiment, the contrast sensitivity is improved in the manner of comparing the electrical signals output from the photodiodes 111a and 111b of the adjacent photodiode cells 110 and controlling switches $S_1$ and $S_2$.

While the configuration is identical to that of the artificial retina system according to the first embodiment, there is a difference in the method for improving the contrast sensitivity. Description of the same elements as those of the artificial retina system according to the first embodiment will be omitted, and only different elements will be described.

First, when light enters the eyeball from the outside, the photodiodes 111a and 111b of each of the photodiode cells 110 output an electric signal corresponding to the magnitude of the introduced light.

The copiers 112a and 112b copy electric signals output from the respective photodiodes 111a and 111b, and the copied electric signals flow into the comparator 220a.

The comparator 220a compares the magnitudes of the two electric signals and the controller 230 closes the switch $S_2$ on the side that outputs a larger electric signal and opens the switch $S_1$ on the side that outputs a smaller electric signal. Among the adjacent photodiode cells 110, one is turned on and the other is turned off, so that the contrast sensitivity can be improved.

3. Artificial Retina System According to Third Embodiment

Figure 11:
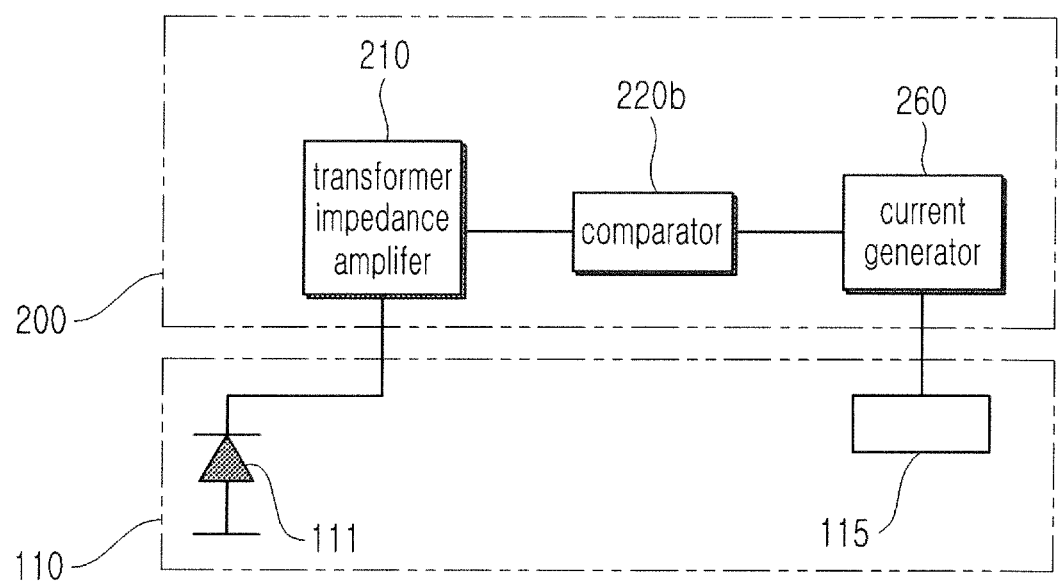
FIG. 11 is a diagram for explaining an operation of an artificial retina system according to still another embodiment of the present invention.

The artificial retina system according to the third embodiment of the present invention will be described with reference to FIG. 11.

The configuration is identical to that of the artificial retina system according to the first embodiment, but there is a difference in that a current generator 260 is additionally provided. The same elements as those of the artificial retina system according to the first embodiment will be omitted, and only different elements will be described.

First, when light enters the eyeball from the outside, the photodiode 111 outputs an electric signal corresponding to the magnitude of the introduced light.

The electric signal output from the photodiode 111 is converted into a voltage signal by the transimpedance amplifier 210, and the converted voltage signal is compared with a plurality of predetermined reference values by the comparator 220b. The current value is determined according to the result of the comparison, and the determined value is input to the current generator 260 to select the biphasic current having various magnitudes stored in advance, and the selected current is output through the stimulation electrode 150. Similarly to the artificial retina system according to the first embodiment, the artificial retina system according to the third embodiment can improve the contrast sensitivity in that the manner of comparing a plurality of reference values with output signals and adjusting the signals output from the stimulus electrodes 150 based on the result of the comparison.

It will be apparent to those skilled in the art that various modifications and variations can be made to the present invention without departing from the spirit and scope of the present invention as defined by the following claims and their equivalents. Accordingly, the scope of protection of the present invention should be determined by the claims.

DESCRIPTION OF THE REFERENCE NUMERALS

100: artificial retina
111: photodiode
112: copier
113: amplifier
114: converter
115: stimulation electrode
200: microcomputer
210: transformer impedance amplifier
220: comparator
230: controller
240: memory
250: communication unit
260: current generator
300: battery
400: external power
500: user input unit
600: external computer
1000: artificial retina system

The invention claimed is:

1. An artificial retina system for improving a contrast sensitivity, comprising:
    an artificial retina configured to be installed under a retina, the artificial retina including a plurality of photodiode cells; and
    a microcomputer configured to compare a magnitude of an electric signal output from a photodiode in each of the photodiode cells with a plurality of reference values and control to amplify or attenuate the electric signal output from each of the photodiode cells according to a result of the comparison,
    wherein each of the photodiode cells includes:
        the photodiode configured to convert light introduced from outside into the electric signal and output the electric signal;
        a copier configured to copy the electric signal output from the photodiode;
        an amplifier configured to amplify or attenuate the electric signal output from the copier; and
        a stimulation electrode configured to stimulate visual cells with the electric signal output from the amplifier,
    wherein the microcomputer adjusts gain of the amplifier to control to amplify or attenuate the electric signal output from the photodiode cell,
    wherein the microcomputer stores a gain value corresponding to a value equal to or greater than one of the plurality of reference values and less than another reference value,
    wherein the visual cells corresponding to each of the photodiode cells are stimulated with an electric signal controlled by the microcomputer.

2. The system of claim 1, wherein each of the photodiode cells further includes a converter configured to cause the electric signal output from each of the photodiode cells to have a form of a biphasic electric signal.

3. The system of claim 1, wherein
    when the number of the plurality of reference values is N, the number of the gain values is NH+1.

4. The system of claim 3, wherein the microcomputer includes:

a transimpedance amplifier configured to convert the electric signal copied by the copier into a voltage signal;

a comparator configured to compare a magnitude of the voltage converted by the transimpedance amplifier with the plurality of reference values;

a controller configured to control the amplifier in accordance with the result of the comparison by the comparator; and a memory configured to store a gain value of the amplifier determined by the controller.

5. The system of claim 1, further comprising:

a user input unit configured to receive a user command; and an external computer configured to execute the microcomputer according to the user command.

6. The system of claim 5, wherein the microcomputer further includes a communication unit configured to wirelessly communicate with the external computer.

7. An artificial retina system for improving a contrast sensitivity, comprising:

an artificial retina configured to be installed under a retina and include a plurality of photodiode cells; and a microcomputer configured to compare a magnitude of an electric signal flowing from a first photodiode of each of the photodiode cells with a magnitude of an electric signal flowing from a second photodiode which is adjacent to the first photodiode, the microcomputer configured to control to amplify or attenuate an electric signal output from each of the photodiode cells in accordance with a result of the comparison, wherein each of the photodiode cells includes:

the photodiode configured to convert light introduced from outside into the electric signal and output the electric signal; and a copier configured to copy the electric signal output from the photodiode, wherein the microcomputer includes:

a comparator configured to compare a magnitude of a copied electric signal output from the first photodiode and a magnitude of a copied electric signal output from the second photodiode; and a controller configured to open a first switch connected to the first photodiode that outputs a first electric signal and wherein the controller is configured to close a second switch connected to the second photodiode that outputs a second electric signal, the second signal being larger than the first signal, and wherein visual cells corresponding to each of the photodiode cells are stimulated with the electric signal controlled by the microcomputer.

8. An artificial retina system for improving a contrast sensitivity, comprising:

an artificial retina configured to be installed under a retina and include a plurality of photodiode cells; and a microcomputer configured to compare a magnitude of an electric signal flowing from a photodiode of each of the photodiode cells with plurality of reference values and controls such that a current is output through a current generator in accordance with a result of the comparison, wherein each of the photodiode cells includes:

the photodiode configured to convert light introduced from outside into the electric signal and output the electric signal; and a stimulation electrode configured to stimulate visual cells with the current generated by the current generator, wherein the microcomputer includes:

a transimpedance amplifier configured to convert the electric signal output from the photodiode into a voltage signal;

a comparator configured to compare the voltage signal converted by the transimpedance amplifier and the plurality of reference values and determine a magnitude of the current according to a comparison result; and the current generator configured to generate the current having the magnitude determined by the comparator and output it through the stimulation electrode, and wherein the visual cells corresponding to each of the photodiode cells are stimulated with the current controlled by the microcomputer.

* * * * *